United States Patent
Moon et al.

(10) Patent No.: US 6,924,402 B2
(45) Date of Patent: Aug. 2, 2005

(54) SIMULTANEOUS PREPARATION OF TETRAFLUOROETHYLENE AND HEXAFLUOROPROPYLENE

(75) Inventors: Dong Ju Moon, Seoul (KR); Jung Jo Jung, Jeonranam-do (KR); Yong Joon Lee, Bucheon-shi (KR); Sang Deuk Lee, Seoul (KR); Byoung Sung Ahn, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 103 days.

(21) Appl. No.: 10/414,740

(22) Filed: Apr. 16, 2003

(65) Prior Publication Data

US 2004/0082822 A1 Apr. 29, 2004

(30) Foreign Application Priority Data

Oct. 23, 2002 (KR) ........................................ 2002-64777

(51) Int. Cl.⁷ .................... C07C 17/02; C07C 17/04; C07C 17/08; C07C 17/00; C07C 21/18
(52) U.S. Cl. ....................................... 570/159; 570/153
(58) Field of Search ................................ 570/153, 159

(56) References Cited

U.S. PATENT DOCUMENTS

| | | | |
|---|---|---|---|
| 2,759,983 A | 8/1956 | Waddell | |
| 3,009,966 A | 11/1961 | Hauptschein et al. | |
| 3,446,858 A | 5/1969 | Shingu et al. | |
| 4,849,554 A | 7/1989 | Cresswell et al. | |

FOREIGN PATENT DOCUMENTS

| | | | |
|---|---|---|---|
| EP | 0287219 B1 | | 5/1992 |
| GB | 904022 | * | 8/1962 |
| GB | 960309 | * | 6/1964 |
| GB | 1041738 | * | 9/1966 |

* cited by examiner

Primary Examiner—Elvis O. Price
(74) Attorney, Agent, or Firm—Jones Day

(57) ABSTRACT

The present invention relates to a process for simultaneously preparing tetrafluoroethylene and hexafluoropropylene by the pyrolysis of difluorochloromethane mixed in the molar ratio of super-heated steam/pre-heated difluorochloromethane ($[H_2O]/[R22]$) of 5–10 under the conditions such as a temperature of 730° C. to 760° C. and a residence time of 0.01 to 0.2 seconds, where the unreacted R22 and produced HFP are recycled and controlled to have an appropriate molar ratio of HFP/R22 of 0.01 to 0.1 in order to obtain a high yield of HFP. Thus, the pyrolysis process of the present invention is efficient for preparing TFE and HFP, which are essential monomers in fluorinated resin industry.

6 Claims, 1 Drawing Sheet

SIMULTANEOUS PREPARATION OF TETRAFLUOROETHYLENE AND HEXAFLUOROPROPYLENE

FIELD OF THE INVENTION

The present invention relates to a process for simultaneously preparing tetrafluoroethylene (TFE) and hexafluoropropylene (HFP) from pyrolysis of difluorochloromethane (R22), and more particularly, to a process for simultaneously preparing tetrafluoroethylene and hexafluoropropylene by pyrolysis of difluorochloromethane mixed in a molar ratio of super-heated steam and pre-heated difluorochloromethane (R22) ($[H_2O]/[R22]$) of 5–10 under the conditions such as a temperature of 730° C. to 760° C. and a residence time of 0.01 to 0.2 seconds, wherein the unreacted R22 and produced HFP are recycled and controlled to have an appropriate molar ratio of HFP/R22 of 0.01 to 0.1 in order to obtain a high yield of HFP. Thus, the pyrolysis process of the present invention is efficient for preparing TFE and HFP, which are essential monomers in fluorinated resin industry.

BACKGROUND OF THE INVENTION

As a monomer for preparing copolymers of fluorinated resins, the demand of HFP has been increased along with TFE. Conventional methods for preparing HFP are pyrolysis of difluorochloromethane($CHClF_2$, R22) (EP Patent No. 0,287,219 (1988) and U.S. Pat. No. 4,849,554 (1989)), pyrolysis of TFE and octafluorocyclobuthane($C_4F_8$, RC318) (U.S. Pat. No. 3,446,858 (1969)), pyrolysis of polytetrafluoroethylene(PTFE) (U.S. Pat. No. 2,759,983 (1956)), and pyrolysis of R23 (U.S. Pat. No. 3,009,966 (1961)).

The process for preparing HFP by pyrolysis of R22 has low selectivity to HFP due to high selectivity of TFE formation and further, it is difficult to separate pure HFP from an azeotropic mixture of R22 and HFP. Pyrolysis of TFE to produce HFP suffers from a low selectivity to HFP because it mainly produces RC318. Pyrolysis of PTFE has a complicate process, wherein TFE is first prepared by pyrolysis of R22 and then, polymerized to produce PTFE, followed by pyrolysis thereof. And further, even if the selectivity to HFP is higher than that from pyrolysis of R22 or TFE, it is an undesirable method because of expensive unit price.

In the process for producing HFP by pyrolysis of R22 according to the present invention, there has been a limitation in a heat supplying rate to efficiently convert R22 to HFP, is improved by supplying steam pre-heated to 530° C. to 580° C. at a steam generator into a super heating unit to generate steam of high temperature above 900° C. to 1000° C. Then, since this high temperature steam is applied for pyrolysis of pre-heated R22, the heat required for pyrolysis is provided. Further, since a reaction is performed at a temperature of 730° C. to 760° C. which is lower than that of conventional reactions, it prevents the formation of byproducts, which may be produced for an exothermic reaction of TFE, and eventually improves the yield of TFE and HFP.

SUMMARY OF THE INVENTION

The inventors have extensively studied to resolve the formation of byproducts associated with pyrolysis of R22 and low selectivity toward HFP. As a result, the present invention provides an efficient process for co-producing TFE and HFP by controlling an appropriate molar ratio between pre-heated R22 and super heated steam and performing the pyrolysis at a relatively low temperature. It further provides a high selectivity of HFP resulted from recycling unreacted R22 and produced HFP mixed in the appropriate ratio for following pyrolysis.

Accordingly, an object of the present invention is to provide a novel process for preparing TFE and HFP simultaneously from pyrolysis of R22.

Another object of the present invention is to provide a method for controlling yield of TFE and HFP selectively.

DETAILED DESCRIPTION OF THE PRESENT INVENTION

Figure 1:
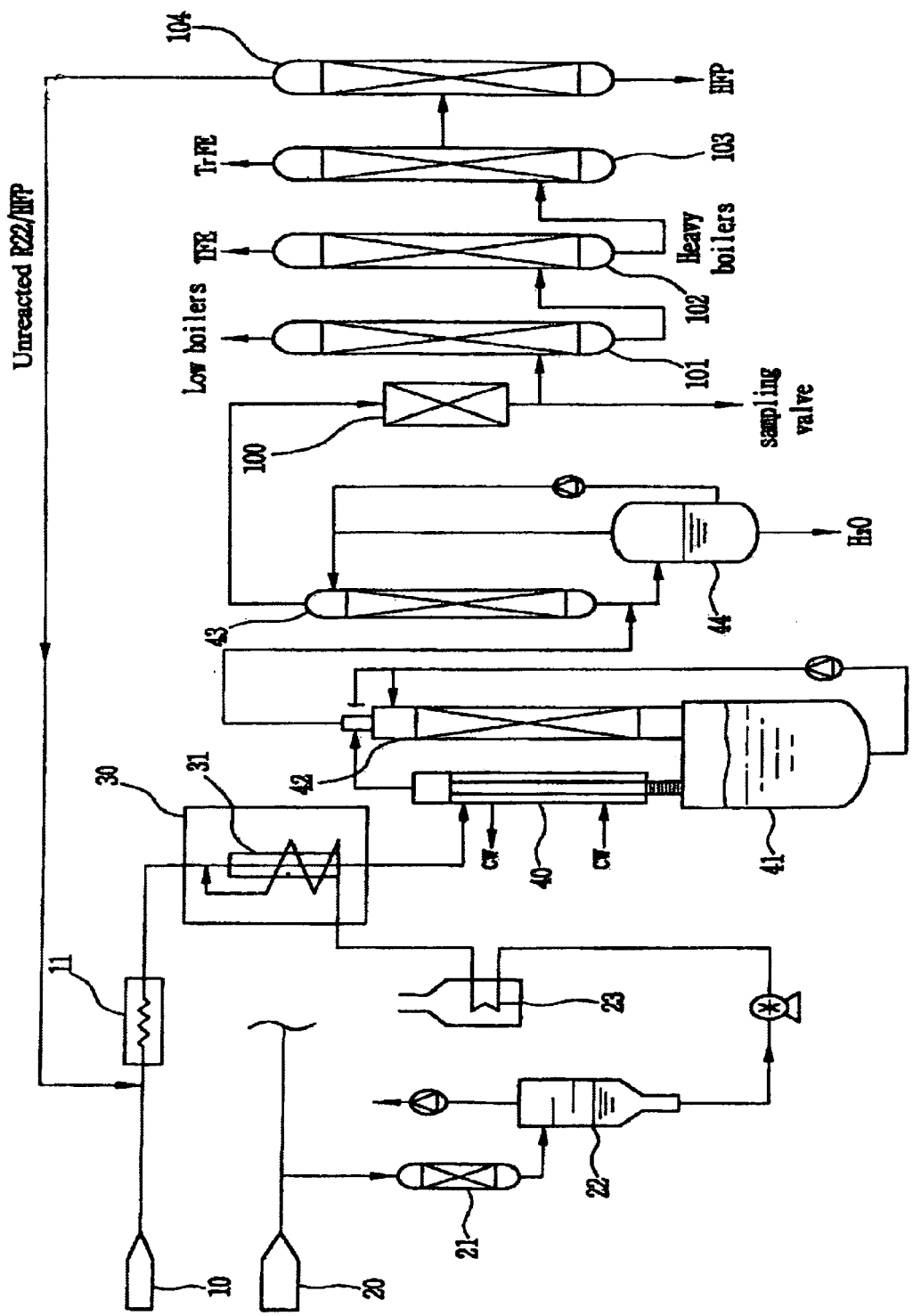
FIG. 1 is a schematic diagram showing the pyrolysis system with the pyrolysis of R22 and the purification and recycling system for industrial applications.

In the present invention, it is characterized by a process for preparing tetrafluoroethylene (TFE) and hexafluoropropylene (HFP) simultaneously comprising the steps of pyrolysis of difluorochloromethane (R22) pre-heated at 150 to 250° C. and super-heated steam under the reaction conditions such as a reaction temperature of 730 to 760° C. and a residence time of 0.01 to 0.2 seconds; and recycling unreacted difluorochloromethane (R22) and produced hexafluoropropylene (HFP) into a pyrolysis reactor, where a molar ratio of difluorochloromethane (R22) and super-heated steam ($[H_2O]/[R22]$) is controlled to be 5 to 10 at the entrance of the reactor and a molar ratio of hexafluoropropylene (HFP) and difluorochloromethane (R22) ($[HFP]/[R22]$) is controlled to be 0.01 to 0.1.

The present invention is described in more detail as set forth hereunder.

The pyrolysis of difluorochloromethane (R22) of the present invention is performed by employing difluorochloromethane (R22) pre-heated to 200° C. and super-heated steam having a temperature of 900 to 1000° C., which is produced by applying steam pre-heated to a temperature of 530 to 550° C. generated by passing a steam generator into a super heating unit. The reactants of super-heated steam and R22 are mixed in an appropriate molar ratio under proper conditions to control a heat supplying rate, which affects the production of TFE and HFP. Further, unreacted R22 and produced HFP are mixed in an appropriate molar ratio and recycled into a pyrolysis reactor to increase a selectivity of HFP. Thus, the present invention exhibits an effective process for preparing TFE and HFP simultaneously, which are essential for the fluorinated resin industry, and increases the selectivity of HFP, which is relatively lower than that of TFE.

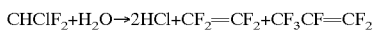

$$CHClF_2+H_2O \rightarrow 2HCl+CF_2=CF_2+CF_3CF=CF_2$$

The pyrolysis of the present invention is performed by employing pre-heated R22 and super-heated steam mixed in the molar ratio ($[H_2O]/[R22]$) of 5 to 10, preferably 7.5 to 8.5. If the steam is not applied or the molar ratio ($[H_2O]/[R22]$) is lower than 5, the conversion to TFE and HFP becomes low as well as the formation of byproducts increases and it requires high cost to separate and purify the products therefrom. On the other hand, if the molar ratio ($[H_2O]/[R22]$) is higher than 10, the production of HFP becomes low and it requires high energy and cost to generate super-heated steam.

In order to control the heat supply rate, which affects the conversion of the reactants to the desired products, R22 is pre-heated to 150 to 250° C. and water is supplied to a steam generator to generate steam of 530 to 550° C. and then, steam is applied into a super heating unit to generate steam of high temperature above 900 to 1000° C. for pyrolysis. Thus, the problematic heat supply rate is resolved by effectively controlling the pre-heated temperature of the reactants and reaction temperature.

The pyrolysis of pre-heated R22 and super-heated steam is performed in the pyrolysis apparatus with an Inconel reactor at a relatively low temperature of 730 to 760° C. If the reaction temperature is below 730° C., the conversion of R22 to the desired products becomes low and the selectivity of HFP also becomes low. On the other hand, if it is above 760° C., the selectivity towards TFE and HFP decreases due to the formation of byproducts resulted from the exothermic reaction of TFE. The pyrolysis of the present invention is performed for a residence time of 0.01 to 0.2 seconds. If the residence time is longer than 0.2 seconds, the selectivity towards TFE and HFP decreases due to the formation of byproducts with prolonged contact time of products and it further, requires high cost to separate and purify the products therefrom.

After the above pyrolysis, unreacted R22 and produced HFP mixed in an appropriate molar ratio are recycled into a pyrolysis reactor to increase the selectivity of HFP. When unreacted R22 and produced HFP are recycled, a molar ratio thereof ([HFP]/[R22]) is in the range of 0.01 to 0.1. If the molar ratio is lower than 0.01, the selectivity of HFP does not increase. On the other hand, if it is higher than 0.1, the selectivity of HFP is not improved due to the formation of byproducts.

The procedure for co-preparing tetrafluoroethylene (TFE) and Hexafluoropropylene (HFP) from pyrolysis of difluorochloromethane (R22) as shown in FIG. 1 is described in more detail by following process:
(i) After R22 is preheated at a preheater and super-heated steam is produced by passing steam, pre-heated to 530 to 680° C. at a steam generator, through a super heating unit (30), these pre-heated R22 and super-heated steam are mixed and performed for pyrolysis at a pyrolysis reactor (31);
(ii) Hydrogen chloride (HCl) is separated from the reaction medium;
(iii) After the acid-removed product is neutralized and dried, tetrafluoroethylene (TFE) is isolated and purified therefrom; and
(iv) Hexafluoropropylene (HFP) is isolated and purified and then, unreacted R22 and produced HFP are recycled to the pyrolysis reactor (31).

The apparatus for the pyrolysis of R22 is comprised with a R22 supplying unit comprising a R22 cylinder (10) and a R22 pre-heater (11); a super-heated steam generating unit comprising a process water cylinder (20), a process water column (21), a process water tank (22), a steam generator (23), and a super heating unit (30); a pyrolysis reactor (31) performing pyrolysis reaction after the pre-heated R22 and the super-heated steam are mixed; a purification unit (40, 41, 42, 43, 44) separating hydrogen chloride (HCl) from the reaction medium; purification units (100, 101, 102, 103, 105) separating TFE, TrFE, R125, HFP from the product; and a recycling unit recycling unreacted R22 and purified HFP.

Further, the pyrolysis reactor (31) of the manufacturing system in FIG. 1 includes a quenching column (40) at the exit thereof to prevent side reactions and to efficiently remove hydrogen chloride produced during the reaction by quenching with water. The quenching column is made of carbon and HCl absorbing column (42) and HCl absorbing reservoir is lined with rubber.

As described above, the pyrolysis according to the present invention provides co-production of TFE and HFP as well as increases the selectivity of HFP.

The following examples are intended to be illustrative of the present invention and should not be construed as limiting the scope of this invention defined by the appended claims.

EXAMPLE 1

Difluorochloromethane (R22) was prepared by Ulsan chemical Co., Ltd., purity thereof was 99.9% proved from GC analysis, and an appropriate amount thereof was supplied for pre-heating by using flowmeter (M605, Meterson, US).

Water used for generating super-heated steam was single distilled water and water supplied into the process water tank (22) was kept for 3 hours under the vacuum to remove oxygen therein. The pressure of the process water tank (22) was maintained at the atmospheric pressure by supplying nitrogen gas from a liquid nitrogen cylinder. The nitrogen gas was supplied at a rate of 20 cc/min into the process water tank (22) to prevent air influx while supplying water therein. An appropriate amount of oxygen-removed water in the process water tank (22) was supplied to a steam generator (23).

As shown in FIG. 1, R22 from a R22 cylinder (10) was pre-heated at a preheater (11) to 200° C. and then, supplied to a pyrolysis reactor (31). Water from a process water cylinder (20) was purified by passing through a process water column (ion exchange column, 21 Kwangsung Scientific Co., Korea) and transferred to a process water tank (22) to remove oxygen therein under the vacuum. The oxygen-removed water was then supplied to a steam generator (23) using a pump to generate steam of 530° C. Steam was applied into a super heating unit (30) to generate steam of high temperature, 900 to 1000° C. and then applied to the reactor (31) for pyrolysis of preheated R22.

After the pyrolysis reaction, hydrogen chloride (HCl) in the reaction medium was separated out as an aqueous hydrogen chloride solution by passing through a quenching column (40) and an absorbing column (42). The separated hydrogen chloride solution was stored in a tank (41). The acid removed product was then passed a neutralization column to remove remained HCl by reacting with 4% NaOH solution. A small amount of the neutralized product taken by a sampling valve was analyzed by gas chromatograph and the product was passed an inert column (101) to remove low boilers and a TFE distillation column (102) to purify TFE. The product at the bottom of the TFE distillation column (102) was separated into TrFE and R125 at the top of the TrFE/R125 column (103) and high boilers at the bottom thereof. Unreacted R22 and produced HFP in the middle of the-TrFE/R125 column (103) was transferred to a distillation column of HFP (104), wherein pure HFP was obtained at the bottom and unreacted R22 and HFP mixed in an appropriate molar ratio was recycled to the pyrolysis reactor for further reaction.

The conversion of R22 and selectivity of TFE and HFP with varied reaction temperatures were analyzed by gas chromatograph under the conditions listed in Table 2 and the result was summarized in Table 1.

TABLE 1

The results for Pyrolysis of R22

| Reactants | | | | Residence | | Selectivity (%) | | | |
|---|---|---|---|---|---|---|---|---|---|
| R22 | Steam | Molar ratio | Temp. | time | Conver- | | | | |
| (kg/h) | (kg/h) | ([H$_2$]/[R22]) | (° C.) | (sec)* | sion (%) | R23 | TFP | HFP | others |
| 2.43 | 5.0 | 9.88 | 730 | 0.11 | 65.24 | — | 95.49 | 1.76 | 2.75 |
| 3.82 | 6.0 | 7.55 | 700 | 0.08 | 50.25 | 0.50 | 98.23 | 0.02 | 1.25 |
| 3.82 | 6.0 | 7.55 | 738 | 0.08 | 70.47 | 0.27 | 98.76 | 0.09 | 0.88 |
| 3.82 | 6.0 | 7.55 | 745 | 0.08 | 74.75 | 0.04 | 98.08 | 1.32 | 0.56 |
| 3.82 | 7.0 | 8.80 | 756 | 0.07 | 80.84 | 0.13 | 98.18 | 1.17 | 0.52 |
| 3.82 | 7.0 | 8.80 | 780 | 0.07 | 81.84 | 0.58 | 80.50 | 1.50 | 17.42 |
| 4.66 | 6.0 | 6.19 | 741 | 0.08 | 70.50 | 0.04 | 98.23 | 1.39 | 0.38 |

*residence time at the entrance of the reactor

TABLE 2

| Category | Conditions for GC analysis |
|---|---|
| GC model | GOW MAC, 550 P |
| Column temperature | 50° C. × 5 min |
| | 5° C./min |
| | 150° C. × 15 min |
| Injection temperature | 150° C. |
| Detection temperature | 200° C. |
| Column material | Porapak Q (10 ft L × 1/8 in. O.D.) |

According to Table 1, the conversion of R22 under the reaction conditions such as a reaction temperature of 730 to 760° C. was higher than 70%. It noted that the conversion increased with increasing reaction temperature and residence time. However, when the reaction temperature was lower than 730° C., the conversion was decreased. Further when the reaction temperature was higher than 760° C., the selectivity of TFE and HFP became declined.

Both conversion of R22 and selectivity of TFE and HFP increased with increasing molar ratio of super-heated steam and pre-heated R22 ([H$_2$O]/[R22]) within the range of from 5 to 10. When the molar ratio was below 5, the production yields of TFE and HFP became inferior because the formation of byproducts increased. Further, when the molar ratio was higher than 10, it consumed high energy to generate super-heated steam.

EXAMPLE 2

The pyrolysis of R22 was performed with the same procedure as that of Example 1 and unreacted R22 and produced HFP from a distillation column (104) for HFP purification were recycled and supplied with fresh R22 from a R22 cylinder (10) into a reactor (31) for further pyrolysis.

The conversion and selectivity resulted from the pyrolysis of fresh R22 supplied from the R22 cylinder and those resulted from the pyrolysis of recycled unreacted R22 and HFP mixed in a controlled molar ratio are summarized in Table 3.

A supplying rate of R22 before recycling is a supplying rate of R22 from the R22 cylinder and that after recycling is a supplying rate of a mixture of R22 from the R22 cylinder and recycled unreacted R22 (R22$_{mix}$).

TABLE 3

| Reactants | | | | | | | | Selectivity (%) | | | |
|---|---|---|---|---|---|---|---|---|---|---|---|
| R22* (kg/h) Recycling | | Steam | [H$_2$O]/ | [HFP]/ | Temp. | Residence | Conver- | | | | |
| Before | After | (kg/h) | [R22] | [R22] | (° C.) | time (sec) | sion (%) | R23 | TFE | HFP | others |
| 3.82 | — | 6.0 | 7.54 | 0.05$^a$ | 738 | 0.098 | 78.63 | 0.04 | 98.08 | 1.32 | 0.56 |
| — | 3.82$^a$ | | | | 74.75 | | | 0.08 | 77.59 | 17.53 | 4.8 |
| 3.82 | — | 7.0 | 8.80 | 0.05$^a$ | 747 | 0.07 | 81.84 | 0.13 | 98.18 | 1.17 | 0.54 |
| — | 3.82$^a$ | | | | 79.05 | | | 0.09 | 79.19 | 17.76 | 2.96 |
| 3.82 | — | 7.0 | 8.80 | 0.04$^b$ | 740 | 0.07 | 75.40 | 0.07 | 98.18 | 1.20 | 0.55 |
| — | 3.82$^b$ | | | | 78.25 | | | 0.07 | 80.05 | 15.25 | 4.03 |

*composition of reactants at the entrance of the reactor,
$^a$R22 92.64 mol %, TFE 2.12 mol %, TrFE 0.12 mol %, HFP 4.99 mol %, others 0.13 mol %
$^b$R22 93.68 mol %, TFE 2.51 mol %, TrFE 0.15 mol %, HFP 3.66 mol %

According to Table 3, the selectivity of HFP in the pyrolysis of R22 mixture increased, when the molar ratio of HFP and R22 ([HFP]/[R22]) at the entrance of the reactor after recycling was in the range of 0.01 to 0.1. This selectivity of HFP was far more improved than that from the pyrolysis of fresh R22.

Therefore, the present invention is to provide an effective process for co-preparing TFE and HFP, which is useful industrially, by pyrolysis of pre-heated R22 and super-heated steam. Further, it exhibits an improved selectivity of HFP by applying unreacted R22 and HFP mixed in an appropriate molar ratio compared to the selectivity of HFP by supplying fresh R22.

What is claimed is:

1. A process for simultaneously preparing tetrafluoroethylene (TFE) and hexafluoropropylene (HFP) comprising the steps of:

performing pyrolysis of difluorochloromethane (R22) pre-heated at 150 to 250° C. with super-heated steam at a temperature of from 730 to 760° C. and a residence time of from 0.01 to 0.2 seconds; and recycling hexafluoropropylene (HFP) produced from said pyrolysis and unreacted difluorochloromethane (R22) to a reactor, wherein a molar ratio of super-heated steam and difluorochloromethane (R22) ($[H_2O]/[R22]$) at an entrance of the reactor is in the range of 5 to 10 and a molar ratio of hexafluoropropylene (HFP) produced from said pyrolysis and unreacted difluorochloromethane (R22) ($[HFP]/[R22]$) is in the range of 0.01 to 0.1.

2. The process for simultaneously preparing tetrafluoroethylene (TFE) and hexafluoropropylene (HFP) of claim 1, wherein said molar ratio of super-heated steam and difluorochloromethane (R22) ($[H_2O]/[R22]$) is in the range of 7.5 to 8.5.

3. The process for simultaneously preparing tetrafluoroethylene (TFE) and hexafluoropropylene (HFP) of claim 1, wherein said super-heated steam is prepared by pre-heating to 530 to 580° C. at a preheater followed by heating to 900 to 1000° C. at a super heating unit.

4. The process for simultaneously preparing tetrafluoroethylene (TFE) and hexafluoropropylene (HFP) of claim 1, wherein the reaction product produced from said pyrolysis is quenched with aqueous HCl solution within 0.1 second.

5. The process for simultaneously preparing tetrafluoroethylene (TFE) and hexafluoropropylene (HFP) of claim 1, wherein said process comprises steps of:

(i) performing pyrolysis of a mixture of difluorochloromethane (R22) pre-heated to 150 to 250° C. and super-heated steam in a reactor;

(ii) removing hydrogen chloride (HCl) from the above reactants of said pyrolysis;

(iii) isolating tetrafluoroethylene (TFE) after acid-removed product is neutralized and dried; and (iv) further isolating hexafluoropropylene (HFP) and recycling unreacted difluorochloromethane (R22) and produced hexafluoropropylene (HFP) to the reactor for further pyrolysis.

6. The process for preparing tetrafluoroethylene (TFE) and hexafluoropropylene (HFP) simultaneously of any one of claims 1 to 5, wherein said pyrolysis is performed in a pyrolysis apparatus comprising a R22 supplying unit comprising a R22 cylinder and R22 pre-heater; a super-heated steam generating unit comprising a process cylinder, a process column, a process tank, a steam generator, and a super heating unit; a pyrolysis reactor performing pyrolysis reaction after the pre-heated R22 and the super-heated steam are mixed; a purification unit separating hydrogen chloride (HCl) from the reaction medium; purification units separating TFE, TrFE, R125, HFP from the product; and a recycling line for recycling unreacted R22 and purified HFP.

* * * * *